United States Patent [19]

Richardson et al.

[11] Patent Number: 4,482,558
[45] Date of Patent: Nov. 13, 1984

[54] ANTIFUNGAL AMIDE AND UREA DERIVATIVES OF (3-AMINO-2-ARYL-2-HYDROXYPROP-1-YL)-1H-1,2,4-TRIAZOLES

[75] Inventors: Kenneth Richardson; Peter J. Whittle, both of Canterbury, England

[73] Assignee: Pfizer Inc., New York, N.Y.

[21] Appl. No.: 500,748

[22] Filed: Jun. 3, 1983

[30] Foreign Application Priority Data

Jun. 18, 1982 [GB] United Kingdom ................ 8217721

[51] Int. Cl.$^3$ .................. A01N 43/64; C07D 249/08; C07D 401/12; C07D 403/12
[52] U.S. Cl. .................................... 424/251; 424/250; 424/263; 424/267; 424/269; 544/298; 544/310; 544/316; 544/317; 544/318; 544/319; 544/321; 544/326; 544/328; 544/331; 544/333; 544/405; 546/210; 546/276; 548/112; 548/229; 548/262
[58] Field of Search ................ 548/262; 544/298, 316, 544/331, 317, 310, 318, 319, 321, 326, 328, 405, 333; 546/210, 276; 424/250, 251, 263, 267, 269

[56] References Cited

FOREIGN PATENT DOCUMENTS 0054974 6/1982 European Pat. Off. ............ 548/341
61835 10/1982 European Pat. Off. ............ 548/262

Primary Examiner—Alton D. Rollins
Attorney, Agent, or Firm—Charles J. Knuth; Albert E. Frost; Paul D. Thomas

[57] ABSTRACT

Compounds of the general formula

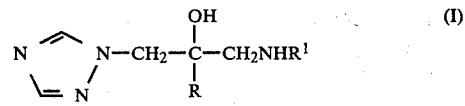

or a pharmaceutically acceptable acid addition salt thereof, wherein R is naphthyl, biphenylyl, phenyl or substituted phenyl; and $R^1$ is

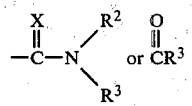

where X is O or S, $R^2$ is H, or $C_1$–$C_4$ alkyl and $R^3$ is H, $C_1$–$C_4$ alkyl, $C_3$–$C_6$ cycloalkyl, optionally mono- or disubstituted phenyl, benzyl or Het and Het is pyridyl, pyrimidinyl or pyrazinyl; said substituents being halo, $CF_3$, $C_1$–$C_4$ alkyl, $C_1$–$C_4$ alkoxy or hydroxy, or $R^2$ and $R^3$ taken together complete a 1-pyrrolidinyl or piperidino ring; methods for their use in combatting fungal infections in plants and animals, including humans; pharmaceutical and agricultural compositions containing them and intermediates useful in their preparation.

12 Claims, No Drawings

ANTIFUNGAL AMIDE AND UREA DERIVATIVES OF (3-AMINO-2-ARYL-2-HYDROXYPROP-1-YL)-1H-1,2,4-TRIAZOLES

BACKGROUND OF THE INVENTION

The invention relates to novel triazole derivatives having antifungal activity which are useful in treatment of fungal infections of plants and animals, including humans.

European Patent Application No. 82,300,888.3, published Oct. 6, 1982 as publication No. 0,061,835, broadly describes a large series of S- and O-ethers of 2-aryl-3-mercapto(or 3-hydroxy)-1-(1H-1,2,4-triazol-1-yl)propan-2-ols, and of the corresponding sulfoxides and sulfones of said mercapto derivatives, as antifungal agents.

Concurrently filed U.S. patent applications of Richardson and Gymer, entitled "Antifungal S-Ethers of 2-Aryl-3-Mercapto-1-(1H-1,2,4-Triazol-1-yl)-Propan-2-Ols and Corresponding Sulfoxides and Sulfones", Richardson, Whittle and Cooper, entitled "Antifungal S-Arylmethyl- and S-Heterocyclylmethyl Ethers of 2-Aryl-3-Mercapto-1-(1H-1,2,4-Triazol-1-yl)Propan-2Ols", and Richardson and Whittle, entitled "Triazole Antifungal Agents", and identified U.S. application Ser. Nos. 479,524; 479,526; and 479,525 (all filed Mar. 28, 1984) respectively, are directed to S-ethers of 2-aryl-3-mercapto-1-(1H-1,2,4-triazol-1-yl)propan-2-ols.

SUMMARY OF THE INVENTION

According to the invention, there are provided compounds of the formula:

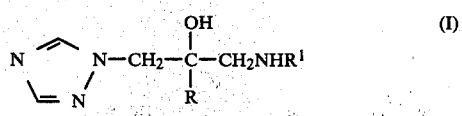
(I)

and their O-esters and O-ethers; wherein R is naphthyl, biphenylyl or phenyl optionally substituted by 1 to 3 substituents each independently selected from halo, $CF_3$, $C_1-C_4$ alkyl and $C_1-C_4$ alkoxy; and $R^1$ is

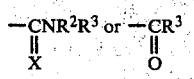

where
X is O or S;
$R^2$ is hydrogen or $C_1-C_4$ alkyl; and
$R^3$ is hydrogen, $C_1-C_4$ alkyl, $C_3-C_6$ cycloalkyl, $R^4R^5C_6H_3(CH_2)_n$, or Het and n is zero or one, $R^4$ and $R^5$ are independently H, halo, $CF_3$, $C_1-C_4$ alkyl or $C_1-C_4$ alkoxy; Het is pyridyl, pyrimidinyl or pyrazinyl, each being optionally monosubstituted or disubstituted by halo, $CF_3$, $C_1-C_4$ alkyl, $C_1-C_4$ alkoxy or hydroxy; or
$R^2$ and $R^3$ taken together with the nitrogen atom to which they are attached represent a 1-pyrrolidinyl or piperidino group; and the pharmaceutically and agriculturally acceptable acid addition salts thereof.

The O-ethers of the alcohols of the formula (I) include, for example, the $C_1-C_6$ alkyl, $C_2-C_4$ alkenyl, $C_2-C_4$ alkynyl, aryl (e.g. phenyl) and aralkyl (e.g. benzyl optionally ring substituted by halo, $C_1-C_4$ alkyl and $C_1-C_4$ alkoxy) ethers.

The O-esters of the alcohols of the formula (I) include, for example, the $C_2-C_4$ alkanoyl and aroyl (e.g. benzoyl, optionally substituted by halo, $C_1-C_4$ alkyl or $C_1-C_4$ alkoxy) esters.

The preferred ester is the acetyl ester.

R is preferably phenyl substituted by 1 or 2 substituents selected from halo, $CF_3$, $C_1-C_4$ alkyl and $C_1-C_4$ alkoxy, most preferably 1 or 2 substituents selected from halo and $CF_3$.

A particularly preferred R is dihalophenyl, especially 2,4-dichlorophenyl.

Preferred as $R^1$ is $R^3CO$ and particularly preferred values of $R^3$ include $C_1-C_4$ alkyl, $R^4$, $R^5C_6H_3(CH_2)_n$ and Het.

Particularly preferred as Het are pyridyl, pyrimidinyl or pyrazinyl each optionally monosubstituted or disubstituted by Cl, $CF_3$ or hydroxy. "Halo" means F, Cl, Br or I.

Where appropriate alkyl and alkoxy groups can be either straight chain or branched chain.

The preferred biphenylyl group is para-bi-phenylyl.

The invention also includes the novel intermediates of the formulae:

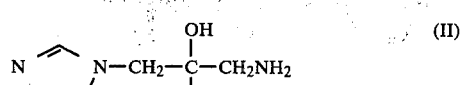

and

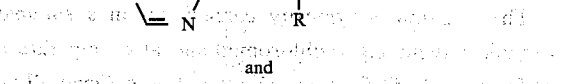

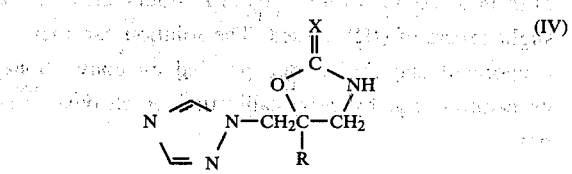

where X is S or O and R is as defined for formula (I).

The invention also provides a pharmaceutical composition comprising an antifungal amount of a compound of the formula (I), or a pharmaceutically acceptable acid addition salt, O-ester or O-ether thereof, together with a pharmaceutically acceptable diluent or carrier. The composition is preferably for human use and in tablet, capsule, injectable or ointment form.

In addition the invention provides a method of treating a fungal infection in an animal, including a human being, in need of such treatment, which comprises administering to said animal an antifungal effective amount of a compound of the formula (I), or a pharmaceutically acceptable acid addition salt, O-ester or O-ether thereof.

The invention yet further provides an agricultural composition suitable for use on a plant or seed comprising an antifungal amount of a compound of the formula (I) or an agriculturally acceptable salt thereof, together with an agriculturally acceptable diluent or carrier.

Also provided is a method of treating a fungal infection in a plant or seed in need of such treatment which comprises administering to said plant or seed an antifungal amount of a compound of the invention.

The invention further provides a compound of the formula (I) or a pharmaceutically acceptable acid addition salt, O-ester or O-ether thereof, for use in treating fungal infections in humans.

Particularly preferred compounds of the invention are compounds of formula (I) wherein R is 2,4- dichlorophenyl and $R^1$ is acetyl, isobutyryl, 4-chlorobenzoyl, 2,4-dichlorobenzoyl, 4-chlorophenylacetyl or 6-chloro-3-pyridylcarbonyl.

DETAILED DESCRIPTION OF THE INVENTION

The ureas and thioureas of the formula (I) can be prepared by the following general methods:

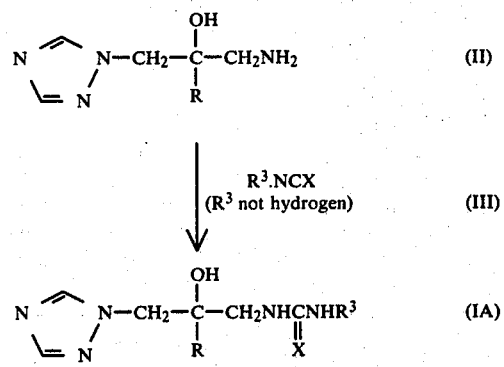

The reaction is typically carried out in a suitable organic solvent, e.g. dichloromethane, at a temperature of from 0°–30° C. for up to about 24 hours. Generally a slight excess of (III) is used. The solution can then be evaporated and the residue purified by conventional procedures, e.g. by recrystallization or chromatography.

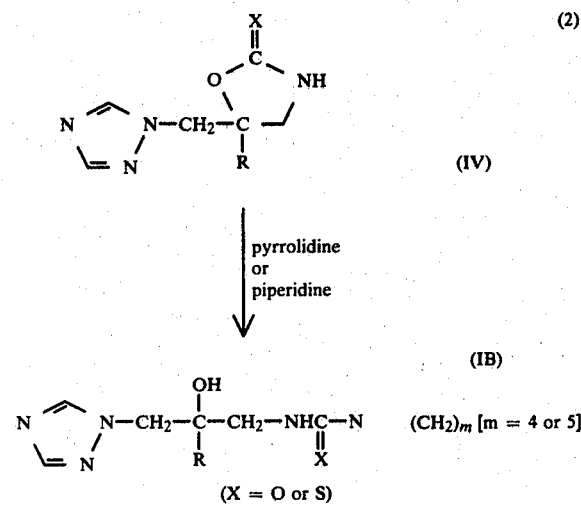

The reaction is typically carried out by heating the 1,3-oxazolidin-2-one or 1,3-oxazolidin-2-thione derivative (IV) with an excess of the appropriate amine either without a solvent or in a suitable organic solvent, e.g. dioxan, for up to about 24 hours. Temperatures up to reflux can be used. The solvent is then evaporated and the residue purified by standard procedures, for example, by column chromatography on silica gel.

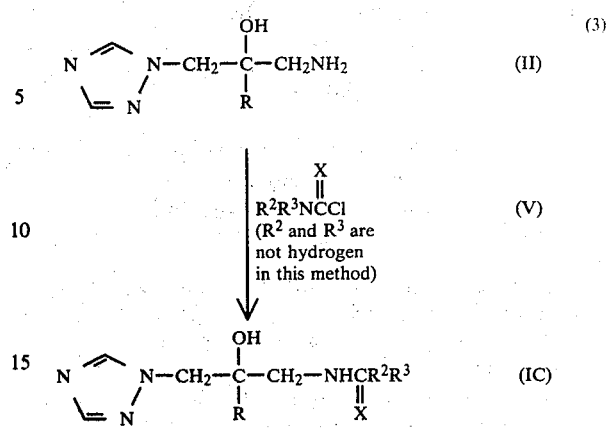

In a typical procedure the amine (II) is dissolved in a suitable organic solvent, e.g. pyridine, with stirring and cooling. The carbamoyl or thiocarbamoyl chloride (V) is then added, generally in a slight excess, and the mixture stirred for up to about 18 hours. Water is then added and the mixture is extracted with a suitable organic solvent, e.g. dichloromethane. The product is recovered from the organic phase and purified, if desired, as described above.

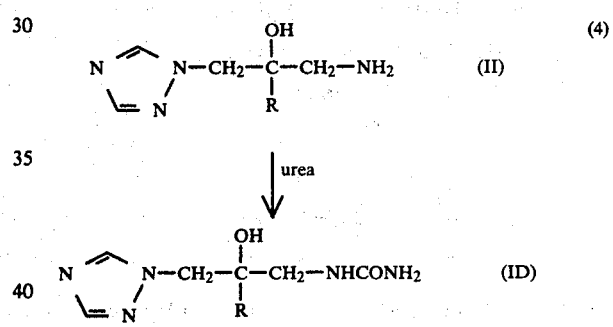

The reaction is preferably carried out under reflux under aqueous acidic conditions for up to about 12 hours, the product again being recovered and purified, if desired, as previously described.

The acylamino derivatives of the formula (I) may be prepared by the following routes:

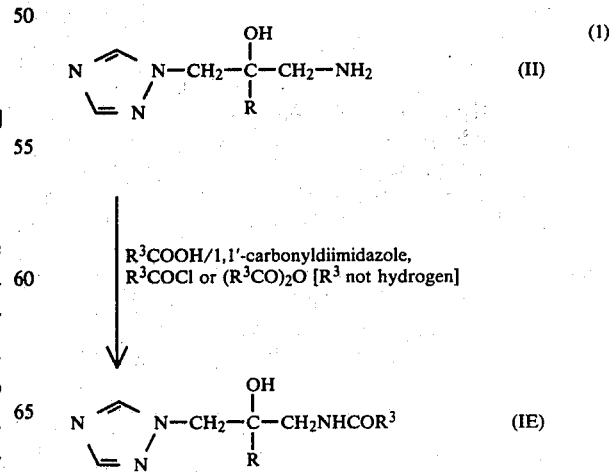

When the free acid, $R^3COOH$, is used, the reaction is typically carried out by heating the acid (generally in slight excess), amine (II) and 1,1'-carbonyldiimidazole at a temperature up to reflux temperature in a suitable organic solvent, e.g. dry tetrahydrofuran (THF), for up to about 6 hours. The solvent is then evaporated, the product recovered from the residue and purified by conventional procedures, for example by crystallization or column chromatography.

When using an acid chloride or anhydride, usually heating is not necessary. Typically the acid chloride or anhydride and amine (II) are stirred in a suitable organic solvent, e.g. dry pyridine, at 0°–5° C. for a few hours, typically 1–2 hours. Water is then added to quench the excess reagent and the mixture is extracted with a suitable organic solvent, e.g. dichloromethane. The product is then recovered from the organic phase and purified, if desired, by methods described above.

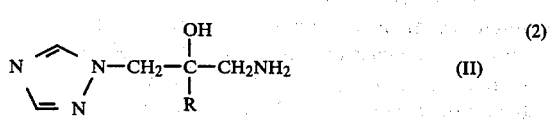 (II)

Formylating agent (e.g. a $C_1$–$C_4$ alkyl formate)

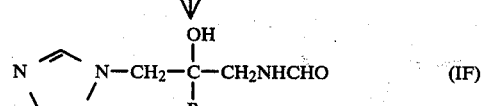 (IF)

The preferred formylating agent is ethyl formate.

Typically the amine (II) and an excess of ethyl formate are heated together under reflux for a few hours.

The product is recovered and purified by conventional procedures, described above.

Other conventional formylating agents such as formic acid/acetic anhydride and dimethylformamide/sodium methoxide, can also be used.

The O-ethers are made by conventional methods, e.g. by treating an alkali metal salt of the alcohols of the formula (I), e.g. a lithium or sodium salt, with the appropriate halide, e.g. an alkyl, alkenyl, alkynyl or aralkyl halide. O-Esters are also made by conventional methods, e.g. by treating an alkali metal salt of compound (I) with an appropriate acid chloride or anhydride.

As will be recognized by one of skill in the art, the compounds of the invention contain at least one optically active center at the 2-position and the invention includes both the resolved and unresolved forms. Resolution can be carried out according to standard techniques.

Pharmaceutically acceptable acid addition salts of the compounds of the formula (I) are generally those formed from strong acids which form non-toxic acid addition salts, such as, e.g., hydrochloric, hydrobromic, sulphuric, oxalic and methanesulfonic acids. These salts can be obtained by conventional methods, e.g. by reaction of equimolar amounts of the free base and the desired acid in an appropriate organic solvent. The salt thus formed is collected by filtration, if insoluble, or by evaporation of solvent. The invention also includes the alkali metal and ammonium salts, which again are formed by conventional methods.

The starting materials for the previous routes are either known compounds or may be prepared conventionally. Typical routes, which are illustrated in detail in the Examples and Preparation, are as follows:

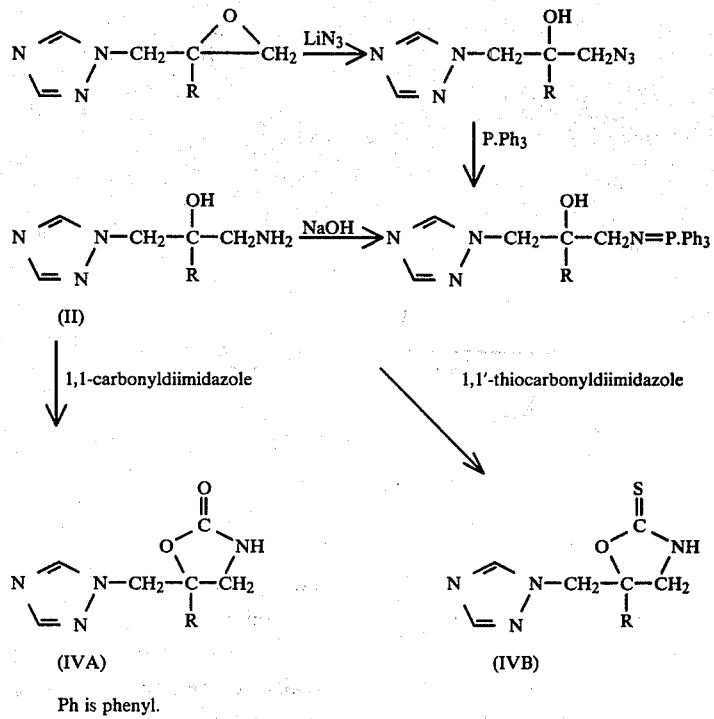

Ph is phenyl.

The compounds of the formula (I) and their salts, O-esters and O-ethers are very active anti-fungal agents, useful in combatting fungal infections in animals, including humans. For example they are useful in treating topical fungal infections in man caused by, among other organisms, species of Candida, Trichophyton, Microsporum, or Epidermophyton, or in mucosal infections caused by *Candida albicans* (e.g thrush and vaginal candidiasis). They may also be used in the treatment of systemic fungal infections caused by, for example, *Candida albicans, Cryptococcus neoformans, Aspergillus fumigatus,* Coccidioides, Paracoccidioides, Histoplasma or Blastomyces.

The in vitro evaluation of the antifungal activity of the compounds can be performed by determining the minimum inhibitory concentration (m.i.c.) which is the lowest concentration of the test compound in a suitable medium at which growth of the particular microorganism fails to occur. In practice, a series of agar plates, each having the test compound incorporated at a particular concentration are inoculated with a standard culture of, for example, *Candida albicans* and each plate is then incubated for 48 hours at 37° C. The plates are then examined for the presence or absence of growth of the fungus and the appropriate m.i.c. value is noted. Other microorganisms used in such tests can include *Cryptococcus neoformans, Aspergillus fumigatus,* Trichophyton spp, Microsporum spp, *Epidermophyton floccosum, Coccidioides immitis,* and *Torulopsis glabrata*.

The in vivo evaluation of the compounds can be carried out at a series of dose levels by intraperitoneal or intravenous injection or by oral administration, to mice which are inoculated with a strain of *Candida albicans.* Untreated mice die within 48 hours and the dose level at which the compound provides 50% protection against the lethal effect of the infection, the $PD_{50}$ in mg/kg, is noted.

The in vivo oral $PD_{50}$ values for selected compounds of formula (I) in mice inoculated with a lethal dose of *Candida albicans,* as described above, are summarized in the table below.

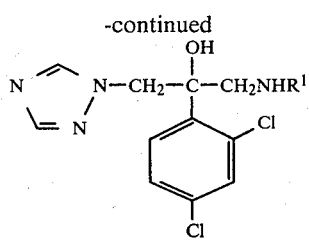

| $R^1$ | Oral $PD_{50}$ (mg/kg) |
|---|---|
| CO—⟨pyridyl⟩—Cl | 1.5 |
| COCH(CH₃)₂ | 4.2 |
| COCH₂—⟨phenyl⟩—Cl | 3.5 |
| CO—⟨2-Cl-phenyl⟩—Cl | 4.2 |
| CO—⟨phenyl⟩—Cl | 1.3 |
| COCH₃ | 2.4 |

For human use, the antifungal compounds of the formula (I) (or salts, esters or ethers thereof) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavoring or coloring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral and parenteral administration to human patients, the daily dosage level of the antifungal compounds of the formula (I) will be from 0.1 to 5 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the antifungal compounds of the formula (I) may be administered in the form of a suppository or pessary, or may be applied topically in the form of a lotion, solution, ointment or dusting powder. For example, they may be incorporated into an ointment consisting of an aqueous emulsion of polyethylene glycols or liquid paraffin; or they may be incorporated, at a concentration of between 1 and 10%, into an ointment consisting of a white wax or white soft paraffin base together with such stabilizers and preservatives as may be required.

The compounds of the formula (I) and their salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Microorganisms used in such tests include *Cochliobolus carbonum, Pyricularia oryzae, Glomerella cingulata, Penicillium digitatum, Botrytis cinerea* and *Rhizoctonia solani*.

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

The following Examples illustrate the invention. All temperatures are in °C. Ratios of solvent mixtures employed for chromatography are by volume.

EXAMPLE 1

N-(4-Chlorobenzyl)-N'-[2-(2,4-dichlorophenyl)-2-hydroxy-3-(1H-1,2,4-triazol-1-yl)prop-1-yl]thiourea

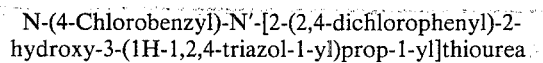

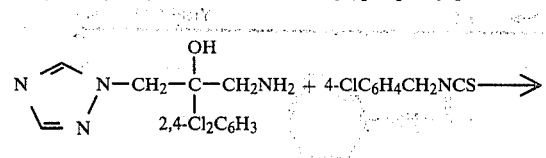

The amine (A) (0.4 g, 1.39 mmole) and 4-chlorobenzylisothiocyanate (0.28 g, 1.53 mmole) were stirred in dichloromethane (20 ml) and the mixture was cooled in an ice-bath. After one hour the ice-bath was removed and stirring was continued for a further 18 hours. Evaporation of solvent and recrystallization from ethanol gave the title compound, 0.55 g (84%), m.p. 209°–210° C.

Analysis %: Found: C, 48.48; H, 4.01; N, 15.09. Calculated for $C_{19}H_{18}Cl_3N_5OS$: C, 48.48; H, 3.85; N, 14.88.

EXAMPLES 2–8

The following compounds were prepared similarly to Example 1, starting from the same amine and appropriate isocyanate or isothiocyanate:

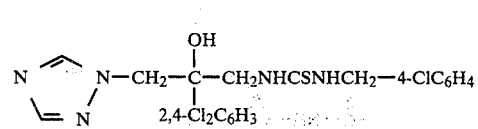

| Example No. | R¹ | Yield (%) | m.p. (°C.) | Analysis (Calculated in brackets) C | H | N |
|---|---|---|---|---|---|---|
| 2 | −C(=S)−NHCH₃ | 66 | 207–208 | 43.41 (43.35 | 4.26 4.20 | 19.96 19.44) |
| 3 | −C(=O)−NHCH₃ | 65 | 166–168 | 45.19 (45.36 | 4.38 4.39 | 20.5 20.35) |
| 4 | −C(=O)−NH−C₆H₄−Cl | 55 | 205–207 | 49.15 (49.06 | 3.76 3.66 | 16.22 15.89) |
| 5 | −C(=S)−NH−cyclopentyl | 59 | 196–198 | 49.13 (49.28 | 4.97 5.10 | 16.96 16.90) |
| 6 | −C(=O)−NH−(3,5-dichloropyridin-2-yl) | 48 | 210–212 | 40.38 (40.28 | 2.87 2.75 | 20.78 20.55) |

-continued

| Example No. | R¹ | Yield (%) | m.p. (°C.) | Analysis (Calculated in brackets) | | |
|---|---|---|---|---|---|---|
| | | | | C | H | N |
| 7 |  | 64 | 195–197 | 46.62 (46.55 | 3.32 3.29 | 14.63 14.28) |
| 8 |  | 60 | 188–190 | 48.24 (48.24 | 3.77 3.81 | 19.99 19.86) |

EXAMPLE 9

N-[2-(2,4-Dichlorophenyl)-2-hydroxy-3-(1H-1,2,4-triazol-1-yl)prop-1-yl]-N',N'-tetramethyleneurea

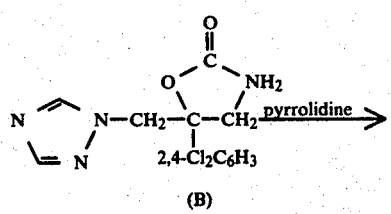

(B)

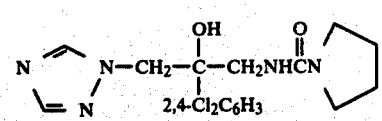

The 1,3-oxazolidin-2-one (B) (0.35 g, 1.12 mmole) and pyrrolidine (0.59 g, 7 mmole) were heated under reflux in dioxan (15 ml) for 18 hours. The solvent was then evaporated and the residue was chromatographed on 230–400 mesh silica, eluting with a mixture of dichloromethane:methanol:28% ammonium hydroxide (98:2:1), to give, after one recrystallization from ethyl acetate, the title compound 0.18 g (42%), m.p. 174°–176° C.

Analysis %: Found: C, 49.71; H, 4.94; N, 18.33. Calculated for C₁₆H₁₉Cl₂N₅O₂: C, 50.01; H, 4.98; N, 18.23.

EXAMPLE 10

N-[2-(2,4-Dichlorophenyl)-2-hydroxy-3-(1H-1,2,4-triazol-1-yl)prop-1-yl]-N',N'-tetramethylenethiourea was prepared similarly to the previous Example, starting from the corresponding oxazolidin-2-thione and pyrrolidine. It had an m.p. of 209°–210° C. (33% yield).

Analysis %: Found: C, 48.09; H, 4.75; N, 17.87. Calculated for C₁₆H₁₉Cl₂N₅OS: C, 48.01; H, 4.78; N, 17.50.

EXAMPLE 11

N-[2-(2,4-Dichlorophenyl)-2-hydroxy-3-(1H-1,2,4-triazol-1-yl)prop-1-yl]-N',N'-dimethylurea

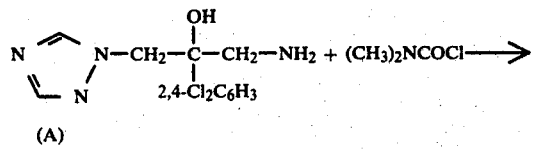

-continued

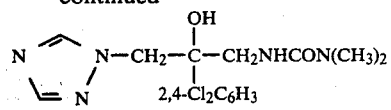

The amine (A) (0.4 g, 1.39 mmole) was dissolved in pyridine (10 ml) and the solution was stirred and cooled in ice. Dimethylcarbamoyl chloride (0.18 g, 1.67 mmole) was then added and stirring was continued for two hours. Water (20 ml) was then added and the mixture was extracted three times with dichloromethane (90 ml in all). The combined extracts were dried (MgSO₄), evaporated and the residue was chromatographed on silica (230–240 mesh), eluting with a mixture of dichloromethane:methanol:28% ammonium hydroxide (93:7:1) to give, after one recrystallization from ethanol, the title compound, 0.29 g (58%), m.p. 189°–190° C.

Analysis %: Found: C, 47.07; H, 4.83; N, 19.87. Calculated for C₁₄H₁₇Cl₂N₅O₂: C, 46.94; H, 4.78; N, 19.55.

EXAMPLE 12

N-[2-(2,4-Dichlorophenyl)-2-hydroxy-3-(1H-1,2,4-triazol-1-yl)prop-1-yl]urea

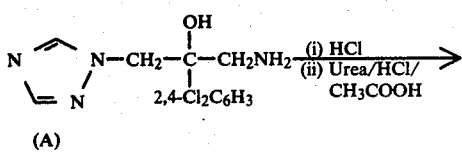

(A)

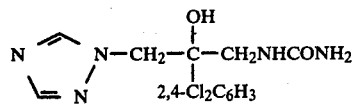

The amine (A) (0.4 g, 1.39 mmole) was dissolved in ether and a solution of hydrogen chloride in ether was added. The solvent was then evaporated and the residue was added to a mixture of urea (0.32 g, 5.3 mmole), water (20 ml), and 24 ml of a mixture of water:concentrated hydrochloric acid:acetic acid (50:1:1). The solution was heated under reflux for 11 hours, allowed to cool and then basified by the addition of solid sodium carbonate. Extraction with ethyl acetate followed by drying (MgSO₄) and evaporation of the combined extracts gave a white glassy solid which was chromatographed on silica (230–240 mesh), eluting with a mixture of dichloromethane:methanol:28% ammonium hydroxide (93:7:1), to give after one recrystallization from ethyl acetate, the title compound, 0.19 g (41%), m.p. 168°–169° C.

Analysis %: Found: C, 43.90; H, 4.01; N, 21.16. Calculated for $C_{12}H_{13}Cl_2N_5O_2$: C, 43.65; H, 3.97; N, 21.21.

EXAMPLE 13

N-[2-(2,4-Dichlorophenyl)-2-hydroxy-3-(1H-1,2,4-triazol-1-yl)-prop-1-yl]-3-pyridinecarboxamide

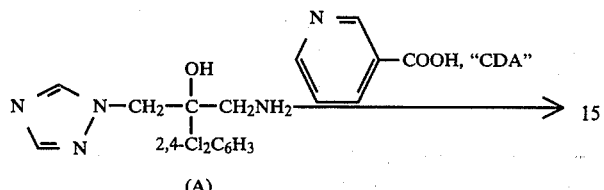

(A)

which was triturated with ethyl ether to give the title compound, 0.54 g (81%), m.p. 175° C. as a colorless solid.

Analysis %: Found: C, 51.94; H, 3.79; N, 18.08. Calculated for $C_{17}H_{15}Cl_2N_5O_2$: C, 52.05; H, 3.85; N, 17.85.

EXAMPLES 14–19

The following compounds were prepared similarly to the previous Example, starting from the same amine, appropriate acid, and "CDA".

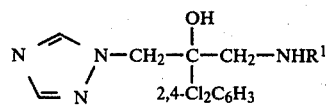

| Example No. | R¹ | Yield (%) | m.p. (°C.) | Analysis % (Calculated in brackets) | | |
|---|---|---|---|---|---|---|
| | | | | C | H | N |
| 14 | -C(=O)-(3-chloropyridin-?) | 81 | 197–198 | 48.08 (47.85) | 3.40 3.30 | 16.70 16.41) |
| 15 | -C(=O)-CH(Me)Me | 62 | 154–155 | 50.37 (50.43) | 5.07 5.08 | 15.69 15.68) |
| 16 | -C(=O)-CH₂-(4-Cl-C₆H₄) | 50 | 150 | 51.76 (51.86) | 3.98 3.89 | 13.06 12.74) |
| 17 | -C(=O)-(2-chloropyridinyl) | 56 | 139–140 | 47.61 (47.85) | 3.33 3.30 | 17.09 16.41) |
| 18 | -C(=O)-pyrazinyl | 53 | 188–189 | 48.87 (48.86) | 3.62 3.59 | 22.08 21.37) |
| 19 | -C(=O)-(6-hydroxypyridinyl) | 55 | 284 with decomp. | 50.08 (50.01) | 3.79 3.70 | 17.41 17.15) |

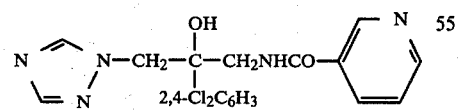

3-Pyridinecarboxylic acid (0.235 g, 1.9 mmole) and 1,1'-carbonyldiimidazole ("CDA") (0.310 g, 1.9 mmole) were dissolved in 10 ml dry tetrahydrofuran (THF). A solution of the amine (A) (0.5 g, 1.74 mmole) in THF (20 ml) was then added and the mixture was heated under reflux for 2 hours. The THF was then evaporated and the residue was dissolved in ethyl acetate. The solution was washed with water (2×100 ml), dried (MgSO₄) and evaporated to give a white glassy solid

EXAMPLE 20

N-[2-(2,4-Dichlorophenyl)-2-hydroxy-3-(1H-1,2,4-triazol-1-yl)prop-1-yl]-2,4-dichlorobenzamide

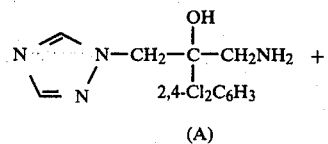

(A)

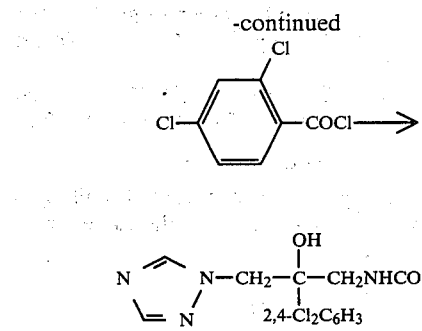

To a stirred and ice-cooled suspension of the amine (A) (0.4 g, 1.39 mmole) in pyridine (10 ml) was added 2,4-dichlorobenzoyl chloride (0.35 g, 1.67 mmole) and stirring was continued for one hour. Water (20 ml) was then added and the mixture was extracted twice with dichloromethane. The combined extracts were dried (MgSO₄) and evaporated to give a yellow oil which was chromatographed on silica (230-400 mesh), eluting first with ethyl acetate and then with a mixture of ethyl ether:ethanol:28% ammonium hydroxide (97:3:1) to give as a white solid, after one recrystallization from ethyl acetate/60°-80° petroleum ether, the title compound, 0.413 g (72%), m.p. 153°–154° C.

Analysis %: Found: C, 46.88; H, 3.05; N, 12.55. Calculated For $C_{18}H_{14}Cl_4N_4O_2$: C, 46.98; H, 3.07; N, 12.18.

EXAMPLE 21

The corresponding 4-chlorobenzamide was prepared similarly to the previous Example, starting from the same amine and 4-chlorobenzoyl chloride. The product had an m.p. of 199°–200° C. (75% yield).

Analysis %: Found: C, 50.96; H, 3.61; N, 13.10. Calculated for $C_{18}H_{15}Cl_3N_4O_2$: C, 50.79; H, 3.55; N, 13.16.

EXAMPLE 22

N-[2-(2,4-Dichlorophenyl)-2-hydroxy-3-(1H-1,2,4-triazol-1-yl)prop-1-yl]acetamide

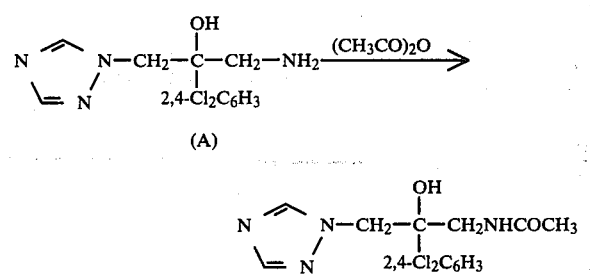

To a stirred and ice-cooled suspension of the amine (A) (0.4 g, 1.39 mmole) in pyridine (10 ml) was added acetic anhydride (0.17 g, 1.67 mmole) and stirring was continued for two hours. Water (20 ml) was then added and the mixture was extracted three times with dichloromethane. The combined extracts were dried (MgSO₄) and evaporated to give a white solid which was recrystallized once from ethyl acetate to give the title compound, 0.27 g (59%), m.p. 178°–179° C.

Analysis %: Found: C, 47.31; H, 4.23; N, 17.20. Calculated for $C_{13}H_{14}Cl_2N_4O_2$: C, 47.43; H, 4.29; N, 17.02.

EXAMPLE 23

N-[2-(2,4-Dichlorophenyl)-2-hydroxy-3-(1H-1,2,4-triazol-1-yl)prop-1-yl]formamide

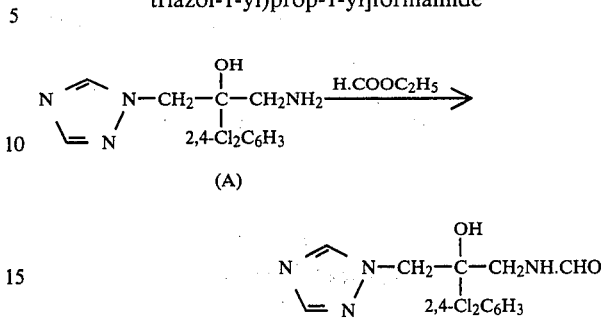

The amine (A) (250 mg) was heated under reflux with excess ethyl formate (10 ml) for 3 hours. The mixture was then cooled and evaporated under reduced pressure to dryness. The residue was triturated with ether to give, as a white solid, the title compound, 253 mg (92%), m.p. 157° C.

Analysis %: Found: C, 45.73; H, 3.83; N, 17.78. Calculated for $C_{12}H_{12}Cl_2N_4O_2$: C, 45.55; H, 3.79; N, 18.09.

EXAMPLE 24

1-[3-Amino-2-(2,4-dichlorophenyl)-2-hydroxyprop-1-yl]-1H-1,2,4-triazole (A)

(a)

1-[3-Azido-2-(2,4-dichlorophenyl)-2-hydroxyprop-1-yl]-1H-1,2,4-triazole (D)

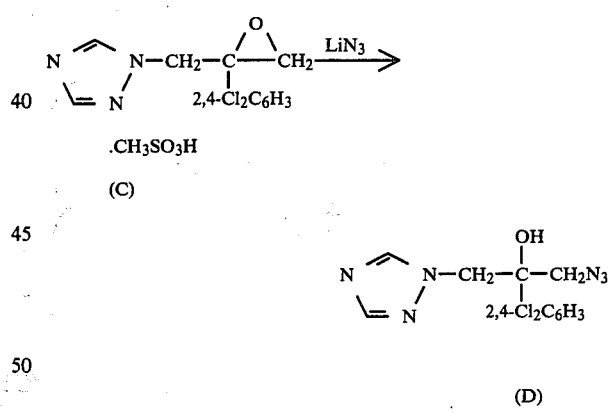

A solution of the epoxide methanesulphonate salt (C) (10 g, 27.32 mmole) and lithium azide (7 g, 143 mmole) in dimethylformamide (100 ml) was stirred at 70° C. for 1.5 hours. The mixture was then cooled and added to a mixture of dichloromethane (500 ml) and water (50 ml). The organic layer was separated and the aqueous layer was washed a further five times with dichloromethane (200 ml in total). The combined organic extracts were dried (MgSO₄) and evaporated to give a colourless gum, trituration of which with ether gave, as a white solid, the title compound, 8.2 g (96%), m.p. 119°–120° C.

Analysis %: Found: C, 42.31; H, 3.23; N, 27.07. Calculated for $C_{11}H_{10}Cl_2N_6O$: C, 42.18; H, 3.22; N, 26.83.

(b) N-[2-(2,4-Dichlorophenyl)-2-hydroxy-3-(1H-1,2,4-triazol-1-yl)-prop-1-yl]triphenylphosphinimine (E)

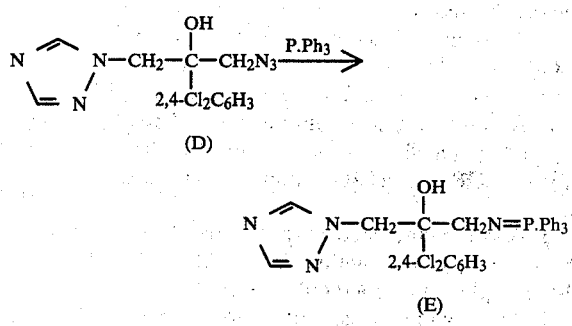

A solution of azide (D) (1 g, 3.2 mmole) and triphenylphosphine (0.84 g, 3.2 mmole) in dichloromethane was stirred at room temperature for 18 hours. Evaporation of solvent and trituration of the residual colourless gum with ether gave, as a white solid, the title compound, (1.72 g, 98%), m.p. 183°–184° C.

Analysis %: Found: C, 63.41; H, 4.59; N, 10.37. Calculated for $C_{29}H_{25}Cl_2N_4OP$: C, 63.6; H, 4.57; N, 10.24.

(c)

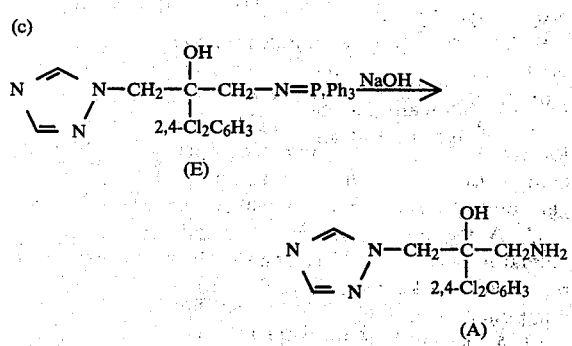

A solution of the phosphinimine (E) (0.5 g, 0.914 mmole) in a mixture of methanol (15 ml) and 1N sodium hydroxide solution (5 ml) was heated under reflux for 1.5 hours. The solution was then allowed to cool and the methanol was removed by evaporation under reduced pressure. 3N hydrochloric acid (6 ml) and toluene (10 ml) were then added and the aqueous layer was separated, washed a further three times with toluene (30 ml in total) and then neutralized by addition of solid sodium bicarbonate. Extraction of this solution with dichloromethane (6×10 ml), drying (MgSO₄) and evaporation of the combined extracts gave, as a white solid, the title compound, 254 mg (97%), m.p. 104°–105° C.

Analysis %: Found: C, 45.97; H, 4.31; N, 19.26. Calculated for $C_{11}H_{12}Cl_2N_4O$: C, 45.99; H, 4.18; N, 19.5.

EXAMPLE 25

5-(2,4-Dichlorophenyl)-5-(1H-1,2,4-triazol-1-yl-methyl)-1,3-oxazolidin-2-one

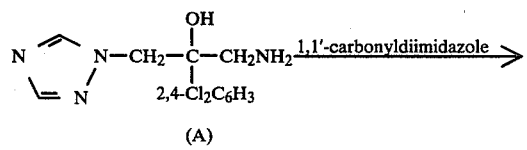

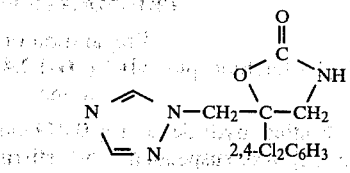

A solution of the amine (A) (0.1 g, 0.35 mmole) and 1,1'-carbonyldiimidazole (0.056 g, 0.35 mmole) in tetrahydrofuran (5 ml) was stirred at room temperature for five hours. The solvent was then evaporated and the residue was dissolved in ethyl acetate (20 ml). This solution was washed three times with water (300 ml total), dried (MgSO₄), evaporated and the residue triturated with a mixture of 60°–80° C. petrol:ether to give, as a white solid, the title compound, 0.074 g (68%), m.p. 223° C.

Analysis %: Found: C, 45.91; H, 3.27; N, 18.09. Calculated for $C_{12}H_{10}Cl_2N_4O_2$: C, 46.02; H, 3.22; N, 17.89.

EXAMPLE 26

5-(2,4-Dichlorophenyl)-5-(1H-1,2,4-triazol-1-yl-methyl)-1,3-oxazolidin-2-thione

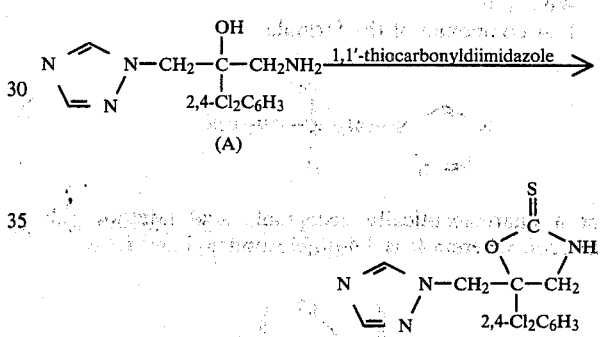

A solution of the amine (A) (1 g, 3.48 mmole) and 1,1'-thiocarbonyldiimidazole (0.62 g, 3.48 mmole) in tetrahydrofuran (20 ml) was stirred at room temperature for one hour. The solvent was then evaporated and the residue was chromatographed on silica (230–400 mesh), eluting with ethyl acetate. One recrystallization from ethanol gave the pure title compound, 0.65 g (57%), as a white solid, m.p. 232°–235° C.

Analysis %: Found: C, 43.95; H, 3.04; N, 17.37. Calculated for $C_{12}H_{10}Cl_2N_4OS$: C, 43.79; H, 3.06; N, 17.02.

EXAMPLE 27

The following illustrate pharmaceutical compositions for the treatment of fungal infections:

(1) Capsule: 71 parts by weight of the compound of Example 14 are granulated with 3 parts maize starch and 22 parts lactose and then a further 3 parts of maize starch and 1 part magnesium stearate are added. The mixture is regranulated and filled into hard gelatin capsules.

(2) Cream: 2 parts by weight of the compound of Example 21 are dissolved in 10 parts of propylene glycol and mixed into 88 parts of a vanishing cream base.

(3) Pessary: 2 parts by weight of the compound of Example 22 are suspended in 98 parts of a warm liquified suppository base which is poured into moulds and allowed to solidify.

PREPARATION 1

Preparation of 2-(2,4-Dichlorophenyl)-2-(1H-1,2,4-triazol-1-ylmethyl)-oxirane Sodium hydride (3.78 g, 0.079 mole as 50% dispersion in oil) was suspended, with stirring, in 20 ml of dry diethyl ether. The ether was then removed by decantation, and the sodium hydride was dried in a stream of dry nitrogen. 100 ml of dry dimethylsulphoxide was added followed by 17.34 (0.079 mole) of dry powdered trimethylsulphoxonium iodide, in portions, over 15 minutes. The resulting mixture was stirred for 30 minutes at room temperature (20° C.). 2-(1H-1,2,4-Triazol-1-yl)-2',4'-dichloro acetophenone (18.33 g, 0.072 mole) as a solution in 50 ml of dry dimethylsulphoxide was then added. The mixture was heated at 60° C. for 3 hours and allowed to stand at room temperature overnight. The reaction mixture was cooled and quenched in ice. The product was then extracted into ethyl acetate (600 ml). The ethyl acetate layer was separated, dried over magnesium sulphate, and concentrated to give a red gum. Column chromatography of the gum on silica, eluting with ether, gave 6.62 g (34.4%) of the title compound as a gum.

We claim:

1. A compound of the formula

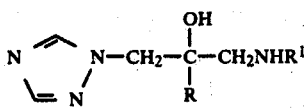

(I)

or a pharmaceutically acceptable acid addition salt thereof, wherein R is 2,4-dichlorophenyl and $R^1$ is

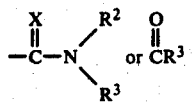

where X is O or S, $R^2$ is H, or $C_1$–$C_4$ alkyl and $R^3$ is H, $C_1$–$C_4$ alkyl, $C_3$–$C_6$ cycloalkyl, $R^4R^5C_6H_3(CH_2)_n$ or Het, and n is zero or one, $R^4$ and $R^5$ are independently H, chloro, or $CF_3$ and Het is pyridyl, pyrimidinyl or pyrazinyl, each being optionally monosubstituted or disubstituted by chloro, $CF_3$ or hydroxy, or when taken together with the nitrogen atom to which they are attached $R^2$ and $R^3$ are 1-pyrrolidinyl or piperidino.

2. A compound according to claim 1 wherein $R^1$ is $COR^3$ and $R^3$ is $C_1$–$C_4$ alkyl, $R^4R^5C_6H_3(CH_2)_n$ or Het; and $R^4$ and $R^5$ are each H, chloro or $CF_3$.

3. A compound according to claim 2 wherein $R^3$ is pyridyl optionally monosubstituted by chloro, $C_1$–$C_4$ alkyl or $R^4R^5C_6H_3(CH_2)_n$ where $R^4$ is H or Cl and $R^5$ is Cl.

4. A compound according to claim 3 wherein $R^3$ is 6-chloro-3-pyridyl, methyl, isopropyl, 4-chlorobenzyl, 4-chlorophenyl or 2,4-dichlorophenyl.

5. The compound according to claim 4: N-[2-(2,4-dichlorophenyl)-2-hydroxy-3-(1H-1,2,4-triazol-1-yl)-prop-1-yl]-6-chloro-3-pyridinecarboxamide.

6. The compound according to claim 4: N-[2-(2,4-dichlorophenyl)-2-hydroxy-3-(1H-1,2,4-triazol-1-yl)-prop-1-yl]-4-chlorophenylacetamide.

7. The compound according to claim 4: N-[2-(2,4-dichlorophenyl)-2-hydroxy-3-(1H-1,2,4-triazol-1-yl)-prop-1-yl]-4-chlorobenzamide.

8. The compound according to claim 4: N-[2-(2,4-dichlorophenyl)-2-hydroxy-3-(1H-1,2,4-triazol-1-yl)-prop-1-yl]acetamide.

9. A pharmaceutical composition comprising an antifungal amount of a compound according to claim 1 and a pharmaceutically acceptable diluent or carrier.

10. An agricultural antifungal composition suitable for use on a plant or seed which comprises an antifungal amount of a compound according to claim 1 and an agriculturally acceptable diluent or carrier.

11. A method of treating a fungal infection in an animal in need of such treatment which comprises administration to said animal of an antifungal amount of a compound according to claim 1.

12. A method of treating a fungal infection in a plant or seed in need of such treatment which comprises administration to said plant or seed of an antifungal amount of a compound according to claim 1.

* * * * *